(12) United States Patent
Patel et al.

(10) Patent No.: US 7,074,931 B2
(45) Date of Patent: Jul. 11, 2006

(54) PROCESS FOR ASYMMETRIC SYNTHESIS OF SUBSTITUTED 1,4-DIHYDROPYRIDINES

(75) Inventors: Ian Patel, Bristol (GB); Ian Ashworth, Stalybridge (GB); Daniel Levin, Poynton (GB)

(73) Assignee: Astrazeneca AB, Sodertalje (SE)

( * ) Notice: Subject to any disclaimer, the term of this patent is extended or adjusted under 35 U.S.C. 154(b) by 324 days.

(21) Appl. No.: 10/333,669

(22) PCT Filed: Jul. 31, 2001

(86) PCT No.: PCT/SE01/01685

§ 371 (c)(1),
(2), (4) Date: Jan. 21, 2003

(87) PCT Pub. No.: WO02/10134

PCT Pub. Date: Feb. 7, 2002

(65) Prior Publication Data

US 2004/0039207 A1 Feb. 26, 2004

(30) Foreign Application Priority Data

Aug. 2, 2000 (GB) .................................. 0018896
Mar. 15, 2001 (SE) .................................. 0100899

(51) Int. Cl.
C07D 211/02 (2006.01)
C07D 215/16 (2006.01)

(52) U.S. Cl. ...................................... 546/153; 546/249

(58) Field of Classification Search ................ 546/153, 546/249
See application file for complete search history.

(56) References Cited

FOREIGN PATENT DOCUMENTS

| DE | 2003148 | 7/1971 |
|----|---------|--------|
| EP | 0429603 B1 | 6/1991 |
| GB | 439195 A | 12/1935 |
| WO | WO9107368 A1 | 5/1991 |
| WO | WO9107371 A1 | 5/1991 |
| WO | WO9408966 A1 | 4/1994 |
| WO | WO9528388 A1 | 10/1995 |
| WO | WO0024743 | 5/2000 |
| WO | WO0051986 A1 | 9/2000 |

*Primary Examiner*—Cecilia J. Tsang
*Assistant Examiner*—Raymond Covington
(74) *Attorney, Agent, or Firm*—Kenneth F. Mitchell; Paul K. Legaard

(57) ABSTRACT

A process is described for reacting a vinylogous amide with an α,β-unsaturated ketone in the presence of a silicon compound to form an 1,5-diketone which is converted to a 1,4-dihydropyridine. Asymmetric substituted 1,4-dihydropyridines are synthesized by the process by preparing an asymmetric vinylogous amide by reacting a 1,3-cyclohexanedione with a substantially homo-chiral phenylethylamine. Reaction of the asymmetric vinylogous amide with an α,β-unsaturated ketone in the presence of a silicon compound forms an asymmetric 1,5-diketone. The 1,5-diketone is converted to an asymmetric substituted 1,4-dihydropyridine.

7 Claims, No Drawings

PROCESS FOR ASYMMETRIC SYNTHESIS OF SUBSTITUTED 1,4 -DIHYDROPYRIDINES

CROSS-REFERENCE TO RELATED APPLICATIONS

This application is the U.S. National Stage filing of International Application Ser. No. PCT/SE01/01685 filed Jul. 31, 2001, which claims priority to Swedish Application No. 0100899-4 filed Mar. 15, 2001 and Great Britain Application No. 0018896.1 filed Aug. 2, 2000.

FIELD OF THE INVENTION

This invention relates to a process for an asymmetric synthesis of substituted 1,4-dihydropyridines useful as smooth muscle relaxants in mammals.

BACKGROUND ART

Inappropriate smooth muscle activation is believed to be involved in urinary incontinence and in many other conditions and diseases including, hypertension, asthma, peripheral vascular disease, right heart failure, congestive heart failure, angina, ischemic heart disease, cerebrovascular disease, renal colic, disorders associated with kidney stones, irritable bowel syndrome, male-patter baldness, premature labor, impotence and peptic ulcers.

It is known that urinary incontinence can occur because uncontrolled or unstable bladder contractions arise in excitable bladder tissue, so-called overactive bladder. Existing treatments for urinary incontinence rely largely on drugs that were originally developed for other indications. One group of such drugs includes the calcium-channel blockers, an example of which is nifedipine (4-(2'-nitrophenyl)-2,6,-dimethyl-3,5-dicarbomethoxy-1,4-dihydropyridine). Such drugs were originally developed and are primarily used as antianginal or antihypertensive cardiovascular agents.

Nifedipine is a member of a class of compounds known as dihydropyridines. Structural requirements for calcium blocking activity by dihydropyridines are now well established. Active compounds described in Chapter 14.1 of the medicinal chemistry text book, Comprehensive Medicinal Chemistry, Volume 3, Edited by John C. Emmett (Pergamon Press 1990), possess a 1,4-dihydropyridine ring with an aryl group at the 4-position and ester groups at the 3- and 5-positions.

A group of 1,4-dihydropyridine derivatives that are said to have strong muscular spasmolytic effects, are disclosed in German Patent DE 2003148. Such compounds include certain 4,6,7,8-tetrahydro-5(1H)-quinolones that possess an ester or keto group at the 3-position. A wide spectrum of pharmacological actions are disclosed for the compounds including strong muscular spasmolytic effects which become evident in the smooth musculature of the gastrointestinal tract, the urogenital tract and the respiratory system. Effects on the heart are also disclosed (a "heart-relieving" effect) with a reduction of the blood pressure of normotonic and hypertonic animals.

Vitolinya et al, Khim.-Farm. Zh., 15(1), 39–42, 1981, have reported that 3-cyano-4-phenyl-2,7,7-trimethyl-4,6,7,8-tetrahydro-5(1H)-quinolone blocks the spasmogenic effect of both acetylcholine and barium chloride on intestinal smooth muscle and has hypotensive properties.

S. M. Jain et al, Indian Journal of Chemistry, Volume 30B, November, 1991, pages 1037–1040, discloses the synthesis and pharmacological screening of certain 9-(substituted phenyl)-1,8-(2H,5H-)-acridinediones. The compounds are disclosed by Jain et al, as having varying degrees of hypotensive, anti-inflammatory and anti-implantation activities.

It is known that potassium channel opening compounds can relax smooth muscle tissue by functioning to open potassium channels. For example, D. A. Nurse et al, British Journal of Urology, (1991), 68, 27–31, disclose that a well known potassium channel opener, cromakalim ((−)-6-cyano-3,4-dydihydro-2,2-dimethyl-trans-4,(2-oxo-1-pyrrolidinyl)-2H-benzo[b]pyran-3-ol), has been found to be effective in a preliminary clinical trial for the treatment of urinary incontinence. Accordingly, it is believed that compounds that function to open potassium channels in bladder cells and thereby relax bladder smooth muscle tissue, can prevent or ameliorate uncontrolled bladder contractions which can cause urinary incontinence. It is also known that urinary incontinence can be caused by uncontrolled or unstable bladder smooth muscle contractions and that potassium-channel opening compounds can cause relaxation of smooth muscle and excitable bladder tissue. Accordingly, U.S. Pat. No. 5,455,253 discloses a group of potassium-channel opening compounds, that is, 4,6,7,8-tetrahydro-5(1H)-quinolones, their use in the treatment of urinary incontinence in mammals (including man), and methods for preparing the compounds and pharmaceutical compositions containing the compounds.

DESCRIPTION OF THE INVENTION

In a main aspect the present invention provides a novel synthetic process for making asymmetric substituted or unsubstituted 1,4-dihydropyridines that is suitable for implementation on an industrial scale.

Particularly, it has been found that an α,β-unsaturated ketone may be used to synthesize a substituted 1,4-dihydropyridine by three process steps. First, a vinylogous amide is prepared by reacting a substituted or unsubstituted 1,3-cyclohexanedione with a substituted or unsubstituted phenylethylamine; second, an α,β-unsaturated ketone is reacted with the vinylogous amide to form a 1,5-diketone, and, third, the 1,5-diketone is converted to a 1,4-dihydropyridine.

Advantageously, it has been found that an α,β-unsaturated ketone may be prepared by the process of the present invention by reacting an aldehyde with a ketone without the use of molecular sieves to effect the reaction of the reactants to form the product molecule. It has been found that an α,β-unsaturated ketone can be prepared by reacting an aldehyde with a ketone. Accordingly, an object of a process of the present invention is the synthesis of α,β-unsaturated ketone by the reaction of an aldehyde with an amine-reagent such as pyrrolidine or another secondary amine such as piperidine or morpholine, or a dialkylamine such as diethylamine in dichloromethane at 0–10° C., followed by the addition of a ketone and then trifluoroacetic acid while maintaining the temperature.

Without intending to be bound by the structures shown, it is envisaged that the formation of an α,β-unsaturated ketone proceeds by the formation of intermediates, as shown in the following scheme:

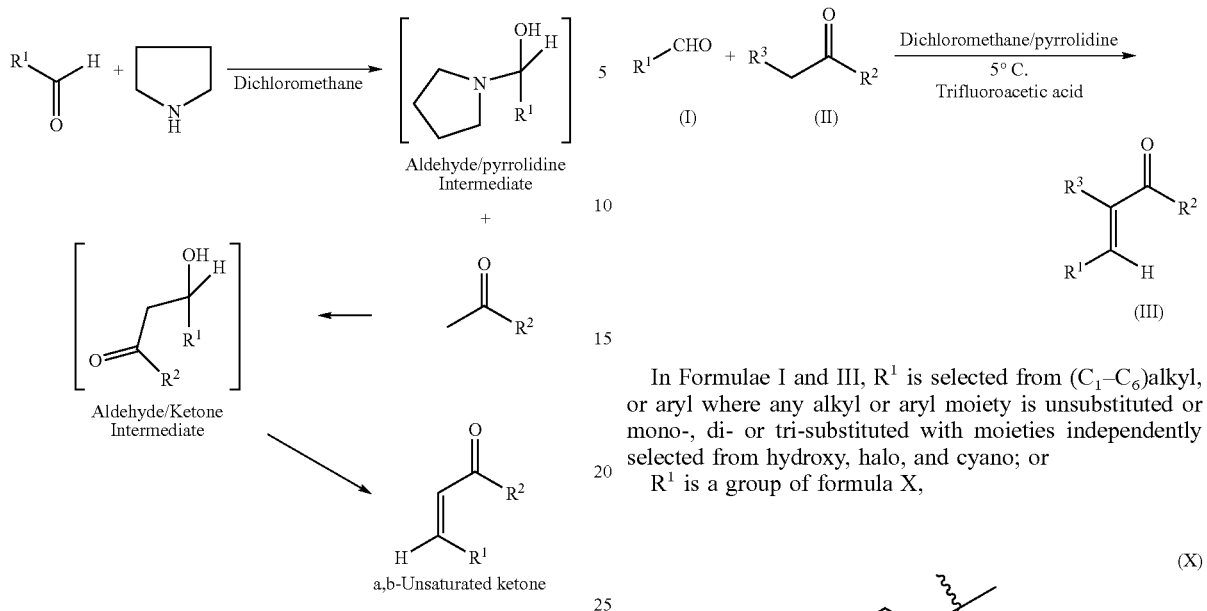

Aldehyde/pyrrolidine Intermediate

Aldehyde/Ketone Intermediate a,b-Unsaturated ketone

It has further been found that an inherently more-efficient process for synthesizing asymmetric vinylogous amides may be achieved by reacting a substituted or unsubstituted substantially homo-chiral phenylethylamine with a substituted or unsubstituted cyclohexanone or 1,3-cyclohexanedione, thereby yielding a substantially homo-chiral vinylogous amide.

Advantageously, it has been found that the reaction of a vinylogous amide with an α,β-unsaturated ketone is facilitated in the presence of a silicon agent. Accordingly, an object of a process of the present invention is the synthesis of a substantially homo-chiral 1,5-diketone useful for making, for example, 1,4-dihydropyridines. Advantageously, the process of the present invention does not require a classical resolution of a racemic mixture as in other routes to this class of compound. These objects and advantages are achieved by the inventive process. Other objects and advantages will be obvious herefrom to those of skill in the art.

Using the process of the present invention, an asymmetric substituted 1,4-dihydropyridine is prepared by reacting a 1,3-cyclohexanedione with a substantially homo-chiral phenylethylamine to yield an asymmetric vinylogous amide; the α,β-unsaturated ketone is then reacted with the asymmetric vinylogous amide to form a 1,5-diketone. Conversion of the 1,5-diketone to a 1,4-dihydropyridine yields a substantially homo-chiral product.

What follows describes the steps of a process for the synthesis of substituted 1,4-dihydropyridines utilizing the present invention.

Step A:

It has been unexpectedly found that when an aldehyde is reacted with a secondary amine such as pyrrolidine in dichloromethane at 0–10° C., followed by the addition of a ketone and then trifluoroacetic acid while maintaining the temperature at −5 to 10° C., an α,β-unsaturated ketone is formed according to the following scheme:

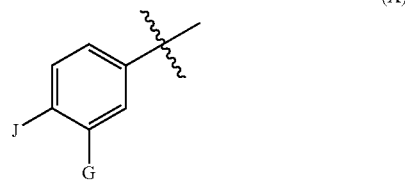

In Formulae I and III, $R^1$ is selected from $(C_1-C_6)$alkyl, or aryl where any alkyl or aryl moiety is unsubstituted or mono-, di- or tri-substituted with moieties independently selected from hydroxy, halo, and cyano; or $R^1$ is a group of formula X, (X)

wherein:

G and J are independently selected from hydrogen, hydroxy $(C_1-C_4)$alkoxy, nitro, cyano, $(C_1-C_4)$fluoroalkyl, $(C_1-C_4)$fluoroalkoxy, halo, $(C_1-C_4)$alkyl, $(C_1-C_4)$alkanoyl, phenyl and $(C_1-C_4)$alkylsulphonyl, or G and J taken together are $(C_1-C_4)$alkylenedioxy; or $R^1$ is 2-thienyl 4-substituted, 5-substituted or 4,5-substituted with E, or 3-thienyl or furyl 5-substituted with E where E is independently selected from a group consisting of nitro, cyano, halo, $(C_1-C_6)$alkyl, $(C_1-C_4)$alkyl-sulphonyl and 2-thienyl; or $R^1$ is a 2-pyridyl 4,5-substituted, 5-substituted or 5,6-substituted with E; or $R^1$ is a 3-pyridyl 6-substituted with E; or $R^1$ is a 4-pyridyl 2-substituted with E.

Particular values of $R^1$ include methyl, ethyl, propyl, iso-propyl, butyl, iso-butyl, sec-butyl, tert-butyl, pentyl, 3-methylbutyl, 1-ethylpropyl, hexyl, 4-methylpentyl, phenyl, 3-methoxyphenyl, 3-nitrophenyl, 3-cyanophenyl, 3-trifluoromethylphenyl, 3-trifluoromethyl-4-cyanophenyl, 4-trifluoromethylphenyl, 3-trifluoromethoxyphenyl, 3-fluorophenyl, 3-chlorophenyl, 3-chloro-4-fluorophenyl, 3-bromophenyl, 4-fluorophenyl, 4-chlorophenyl, 3-bromo-4-fluorophenyl, 3,4-dichlorophenyl, 4-methylphenyl, and 3,4-methylenedioxyphenyl.

Particular values of G include the particular values of J and ethanoyl.

Particular values of J include hydrogen, hydroxy, methoxy, nitro, cyano, trifluoromethyl, trifluoromethoxy, methyl, ethyl, iso-propyl and halo.

Particularly $R^1$ is 3-nitrophenyl or 3-cyanophenyl, and most preferably, $R^1$ is 3-cyanophenyl.

Particular values of substituted 2-thienyl, 3-thienyl or furyl moieties include 4-bromo-2-thienyl, 5-bromo-2-thienyl, 5-methylsulphonyl-2-thienyl, 5-methyl-2-thienyl, 5-(2- thienyl)-2-thienyl, 4-nitro-2-thienyl, 5-nitro-2-thienyl, 4-cyano-2-thienyl, and 5-nitro-3-thienyl.

In formulae I, II and III $R^2$ is hydrogen, $(C_1-C_6)$alkyl or mono-, di- or tri-halo$(C_1-C_4)$alkyl.

Particularly $R^2$ is methyl, ethyl, propyl, iso-propyl, butyl, iso-butyl, sec-butyl, tert-butyl or trifluoromethyl; and most preferably, $R^2$ is trifluoromethyl.

In formulae II and III, $R^3$ is hydrogen, cyano, $(C_1-C_6)$alkyl, $(C_1-C_6)$fluoroalkyl or ethanoyl and preferably $R^3$ is hydrogen.

In formulae II and III, $R^2$ and $R^3$, when taken together, can form a substituted or unsubstituted $(C_1-C_6)$cycloalkyl moiety where particularly $R^2$ and $R^3$, when taken together are 1,4-butandiyl.

Step B:

A vinylogous amide is prepared by reacting a 1,3-cyclohexanedione with a phenylethylamine, at reflux under Dean-Stark conditions. The vinylogous amide is isolated by evaporation of the volatile components of the reaction mixture.

Particularly, it has been found that cyclohexanone, 1,3-cyclohexanedione and substituted-cyclohexanone moieties may be used in the present process together with phenylethylamine, substituted-phenylethylamines and substantally homo-chiral phenylethylamines.

Accordingly, performance of Step B with a substantially homo-chiral phenylethylamine, e.g., (R)-(+)-1-phenylethylamine, yields an asymmetric vinylogous amide according to the following scheme:

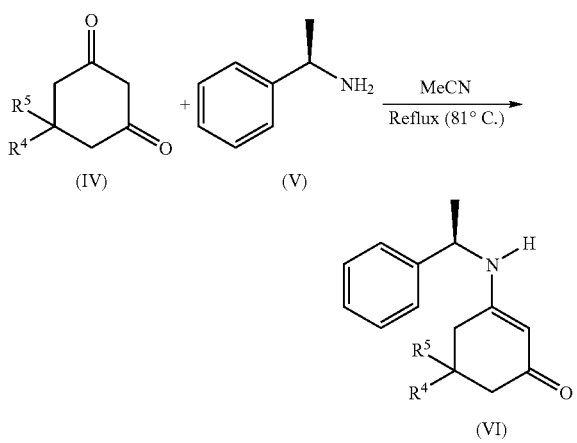

In formulae IV and VI, $R^4$ and $R^5$ are independently selected from hydrogen or $(C_1-C_4)$alkyl.

Particularly, in formulae IV and VI $R^4$ and $R^5$ are independently selected from hydrogen or methyl, and most particularly, $R^4$ and $R^5$ are hydrogen.

Step C:

Vinylogous amides are generally relatively unreactive, however, it has unexpectedly been found that in the presence of a silicon agent capable of acting as a Lewis acid, reaction of a vinylogous amide with an α,β-unsaturated ketone is facilitated with the formation of a 1,5-diketone. A silicon agent suitable to achieve this reaction is trimethylsilyl chloride. Other silicon agents suitable for use in the present invention are triethylsilyl chloride; triphenylsilyl chloride, trimethylsilyltriflate and tributylsilyl chloride.

Accordingly, it has been found that an asymmetric 1,5-diketone can be made by preparing a solution of an α,β-unsaturated ketone and trimethylsilyl chloride in acetonitrile and treating the mixture with an asymmetric vinylogous amide according to the following scheme:

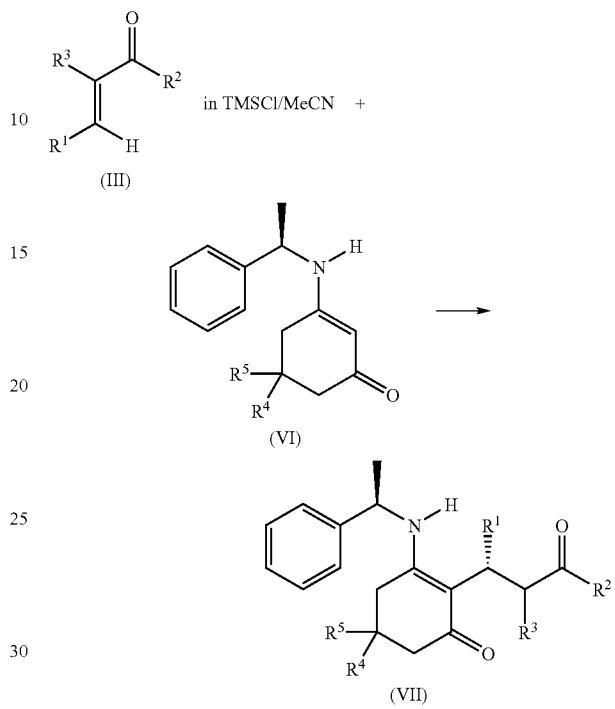

In formulae III, VI and VII, $R^1$, $R^2$, $R^3$, $R^4$ and $R^5$ have the values disclosed heretofore.

Without intending to be bound by theory, it is envisaged that in the process of Step C, an α,β-unsaturated ketone in the presence of a trimethylsilyl chloride reacts with an asymmetric vinylogous amide to yield an intermediate of formula XI which rearranges to another intermediate of formula XII, as shown below:

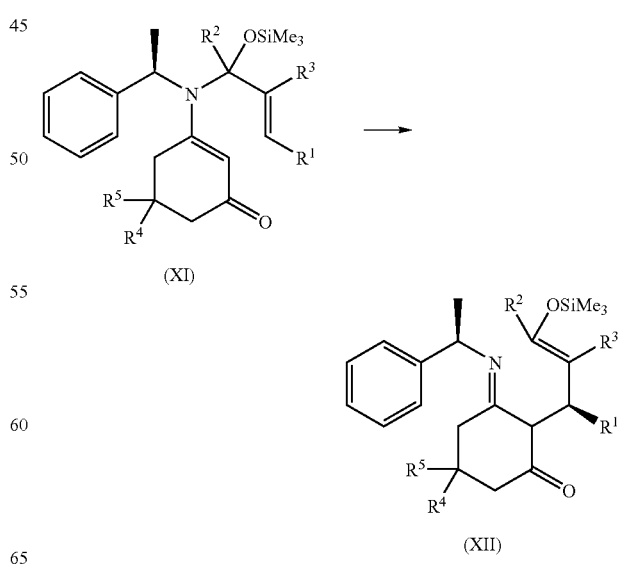

The intermediate, XII, is then believed to convert to the 1,5-diketone product of formula VII, as follows:

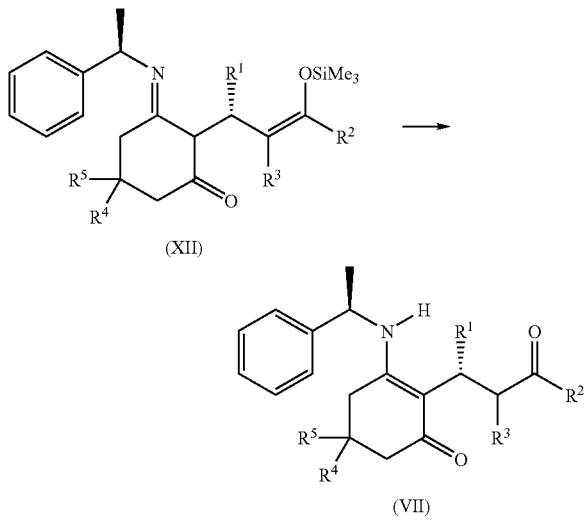

Step D:

A 1,5-diketone is converted to a hemiaminal by treatment with aqueous ammonia in acetonitrile. The hemiaminal is then converted to a 1,4-dihydropyridine by treatment with concentrated hydrochloric acid according to the following scheme:

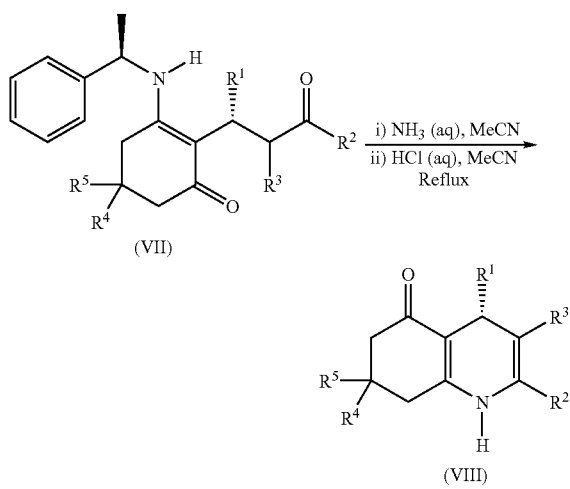

While aqueous ammonia is preferred, it is envisaged that conversion of a 1,5-diketone to a hemiaminal in Step D may otherwise be achieved by use of liquid or gaseous ammonia.

More particularly, the present invention provides a process or method for making 1,4-dihydropyridine compounds, the process comprising:

a) forming a substituted or unsubstituted substantially homo-chiral vinylogous amide by:
 (i) dissolving a substituted or unsubstituted cyclohexanone and a substituted or unsubstituted substantially homo-chiral phenylethyamine in acetonitrile;
 (ii) refluxing to remove water so as to form the vinylogous amide, and
 (iii) isolating the vinylogous amide by evaporating volatile materials;
b) forming a substituted or unsubstituted α,β-unsaturated ketone by:
 (iv) reacting an aldehyde with a amine-reagent selected from pyrrolidine, piperidine, morpholine and diethylaminepyrrolidine in dichloromethane at a temperature of 0–10° C. to form an intermediate, and
 (v) reacting the intermediate with a substituted or unsubstituted ketone by adding trifluoroacetic acid while maintaining a temperature at 0–10° C., to form the α,β-unsaturated ketone;
c) dissolving the vinylogous amide in acetonitrile inerted under nitrogen at a temperature about 25° C.;
d) adding a silicon reagent selected from: trimethylsilyl chloride, triethylsilyl chloride; triphenylsilyl chloride, trimethylsilyltriflate and tributylsilyl chloride over 25–40 minutes while maintaining the temperature at about 25° C. to form a reaction mixture and maintaining the temperature at about 25° C. for about 30 minutes;
e) cooling the reaction mixture to a temperature about 4–10° C. and adding the α,β-unsaturated ketone dissolved in acetonitrile inerted under nitrogen over 25–40 minutes while maintaining the temperature;
f) maintaining the reaction mixture at 5° C. for 5–10 hours, then heating to and maintaining at 24–28° C. for 17–24 hours and further heating to and maintaining at 40–45° C. for 6–10 hours;
g) cooling the reaction mixture to 8–15° C. and adding ammonia over 30–60 minutes;
h) heating the reaction mixture to 50–90° C. for about 17 hours in a pressure vessel;
i) recovering the acetonitrile phase and adding an acid selected from: methane-sulfonic acid, trifluoroacetic acid, acetic acid, para-toluene sulfonic acid, AMBERLYST™ 15 (ion exchange resin), and concentrated hydrochloric acid over 25–40 minutes while maintaining a temperature of 10–25° C. followed by heating to reflux to form a substituted or unsubstituted 1,4-dihydropyridine.

In a particular aspect of the process the amine-reagent is pyrrolidine, the silicon reagent is trimethylsilyl chloride, the ammonia is ammonia in an aqueous solution of ammonium chloride, and the acid is concentrated hydrochloric acid.

In another particular aspect of the process in step d) the solution is added over 30 minutes and the temperature is maintained at 25° C.; in step e) the reaction mixture is cooled to 5° C. and the α,β-unsaturated ketone is added over 30 minutes; in step f) the reaction mixture is maintained at 5° C. for 5 hours, then heated to 26° C. for 17 hours and finally heated to 43° C. for 6 hours; in step g) the reaction mixture is cooled to 10° C. and the ammonia is added over 30 minutes; in step h) the reaction mixture is heated to 80° C. for 17 hours in a pressure vessel, and, in step i) the acid is added over 30 minutes.

In a particular aspect of the process the aldehyde is a compound of formula I

wherein:
R¹ is selected from (C₁–C₆)alkyl, or aryl where any alkyl or aryl moiety is unsubstituted or mono-, di- or tri-substituted with moieties independently selected from hydroxy, halo, and cyano; or $R^1$ is a group of formula X,

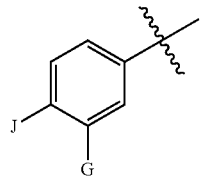

wherein:

G and J are independently selected from hydrogen, hydroxy ($C_1$–$C_4$)alkoxy, nitro, cyano, ($C_1$–$C_4$)fluoroalkyl, ($C_1$–$C_4$)fluoroalkoxy, halo, ($C_1$–$C_4$)alkyl, ($C_1$–$C_4$)alkanoyl, phenyl and ($C_1$–$C_4$)alkylsulphonyl, or G and J taken together are ($C_1$–$C_4$)alkylenedioxy; or $R^1$ is 2-thienyl 4-substituted, 5-substituted or 4,5-substituted with E, or 3-thienyl or furyl 5-substituted with E where E is independently selected from a group consisting of nitro, cyano, halo, ($C_1$–$C_6$)alkyl, ($C_1$–$C_4$)alkyl-sulphonyl and 2-thienyl, where "halo" includes bromo, chloro, fluoro and iodo; or $R^1$ is a 2-pyridyl 4,5-substituted, 5-substituted or 5,6-substituted with E; or $R^1$ is a 3-pyridyl 6-substituted with E; or $R^1$ is a 4-pyridyl 2-substituted with E;

the ketone is a compound of formula II,

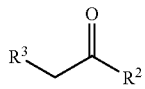

wherein:

$R^2$ is selected from hydrogen, ($C_1$–$C_6$)alkyl and mono-, di- or tri-halo($C_1$–$C_4$)alkyl;

$R^3$ is selected from hydrogen, cyano, ($C_1$–$C_6$)alkyl, ($C_1$–$C_6$)fluoroalkyl and ethanoyl; or $R^2$ and $R^3$, when taken together, form a substituted or unsubstituted ($C_1$–$C_6$)cycloalkyl moiety;

the cyclohexanone is a compound of formula IV,

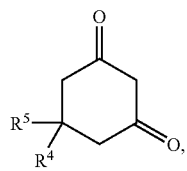

wherein:

$R^4$ and $R^5$ are independently selected from H and ($C_1$–$C_4$) alkyl, and the substantially homo-chiral phenylethylamine is a compound of formula V,

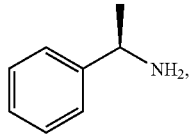

In a more particular aspect of the process, $R^1$ is selected from ($C_1$–$C_6$)alkyl, or aryl where any foregoing alkyl or aryl moiety can be substituted with hydroxy, halo, or cyano; $R^2$ is selected from mono-, di- or tri-halo($C_1$–$C_4$)alkyl; $R^3$ is selected from hydrogen, cyano, ($C_1$–$C_6$)alkyl, ($C_1$–$C_6$)fluoroalkyl and ethanoyl, and $R^4$ and $R^5$ are independently selected from hydrogen or methyl.

In a still more particular aspect of the process $R^1$ is selected from methyl, ethyl, propyl, iso-propyl, butyl, iso-butyl, sec-butyl, tert-butyl, pentyl, 3-methylbutyl, 1-ethylpropyl, hexyl, 4-methylpentyl, phenyl, 3-methoxyphenyl, 3-nitrophenyl, 3-cyanophenyl, 3-trifluoromethylphenyl, 3-trifluoromethyl-4-cyanophenyl, 4-trifluoromethylphenyl, 3-trifluoromethoxyphenyl, 3-fluorophenyl, 3-chlorophenyl, 3-chloro-4-fluorophenyl, 3-bromophenyl, 4-fluorophenyl, 4-chlorophenyl, 3-bromo-4-fluorophenyl, 3,4-dichlorophenyl, 4-methylphenyl, and 3,4-methylenedioxyphenyl; $R^2$ is selected from methyl, ethyl, propyl, iso-propyl, butyl, iso-butyl, sec-butyl, tert-butyl and trifluoromethyl; $R^3$ is selected from hydrogen, cyano and ethanoyl, and $R^4$ and $R^5$ are selected from hydrogen and methyl.

In a most particular aspect of the process $R^1$ is 3-cyanobenzaldehyde; $R^2$ is trifluoromethyl, and $R^3$, $R^4$ and $R^5$ are hydrogen.

It will be appreciated by those of skill in the art that the invention described herein provides a novel process for making α,β-unsaturated ketones that may be utilized in the synthesis of compounds for which an α,β-unsaturated ketone is an intermediate or a precursor. It will also be appreciated that the invention also provides a novel process for the synthesis of an asymmetric product by achieving the reaction of normally-unreactive asymmetric vinylogous amides with α,β-unsaturated ketones. Accordingly, it will be further appreciated that by employing a substantially homo-chiral substituted phenylethylamine, either (R) or (S), to form the vinylogous amide, the desired enantiomeric form of the 1,4-dihydropyridine product, may be determined. For example, if a substituted (R)-phenylethylamine is used, the 1,4-dihydropyridine produced has an (S) configuration.

While not intending to be bound by theory, it is believed that compounds made by the process of the present invention function to prevent or ameliorate uncontrolled bladder contractions, which can cause urinary incontinence, by opening potassium channels in bladder cells and thereby relax bladder smooth muscle tissue. Compounds made by the process of the present invention are therefore useful for relaxing bladder smooth muscle, thus preventing or ameliorating overactive bladder uncontrolled or unstable bladder contractions. Hence, the process of the present invention can be used to make compounds useful for the treatment of urge incontinence, which includes for example detrusor instability, which may result from cystitis, urethritis, tumors, stones, diverticuli or outflow obstruction; and detrusor hyperreflexia, which may result from stroke, dementia, Parkinson's disease, suprasacral spinal cord injury or suprasacral spinal cord disease. Some compounds that can be made by the present process have been found to possess the further unexpected property that they are capable of acting selectively on the bladder without at the same time significantly affecting the cardiovascular system, as indicated by heart rate and blood pressure measurements. Thus, these compounds may be particularly useful to treat urinary incontinence in patients, such as for example the elderly, for whom cardiovascular effects, such as a hypotensive effect, are particularly undesirable.

Thus, this invention provides to a novel process for making a group of compounds which are useful in the treatment of bladder instability in mammals such as man and for the treatment of urinary incontinence in mammals including man.

Particularly, this invention provides a novel process for making 1,4-dihydropyridines of formula VIII. It will be appreciated by those of skill in the art, that compounds of formula VIII contain an asymmetric center, and, accordingly, may exist as, and be isolated as, optically-active and racemic forms. The present invention encompasses a method for making a substantially enantiomerically-pure form of such compounds. Such enantiomerically-pure compounds possess properties useful in the treatment of urinary incontinence, it being well known in the art how to determine efficacy for the treatment of urinary incontinence by standard tests. A description of such tests can be found in U.S. Pat. No. 5,455,253, the disclosure of which is incorporated herein by reference in its entirety.

Definitions:

As used herein, the terms "alkyl" and "alkoxy" include both straight and branched chain radicals, but it is to be understood that references to individual radicals such as "propyl" or "propoxy" embrace only the straight chain ("normal") radical, branched chain isomers such as "iso-propyl" or "iso-propoxy" being referred to specifically.

As used herein "halo" includes fluoro, chloro, bromo, and iodo unless noted otherwise.

When used herein in the disclosure and the claims, ranges as applied to temperatures, concentrations, times, values etc., whether disclosed as "10–25," "1 to 110" or the like, are to be read to include all integral, and where appropriate non-integral, values within the stated range.

Particular values of $(C_1-C_4)$alkyl include methyl, ethyl, propyl, iso-propyl, butyl, iso-butyl, sec-butyl, and tert-butyl.

Particular values of $(C_1-C_4)$fluoroalkyl include trifluoromethyl and pentafluoroethyl.

Particular values of $(C_1-C_4)$alkoxy include methoxy, ethoxy, propoxy, iso-propoxy, butoxy, iso-butoxy, sec-butoxy, and tert-butoxy.

Particular values of $(C_1-C_4)$fluoroalkoxy include trifluoromethoxy and pentafluoroethoxy.

A particular value of $(C_1-C_4)$alkanoyl is ethanoyl.

A particular value of $(C_1-C_4)$alkylsulphonyl is methanesulphonyl.

Particular values for $(C_1-C_3)$alkylenedioxy are methylenedioxy and ethylenedioxy.

EXAMPLES

The following examples illustrate how a process according to the present invention is carried out and how substantially enantiomerically-pure forms of 1,4-dihydropyridines can be made with the present invention. The examples provided herein are exemplary and are not to be regarded as limiting the scope of the invention.

Example 1

3-(4,4,4-Trifluoro-3-oxo-1-butenyl)benzonitrile 3-(4,4,4-Trifluoro-3-oxo-1-butenyl)benzonitrile, (an α,β-unsaturated ketone) was made by reacting 3-cyanobenzaldehyde of formula Ia with 1,1,1-trifluoroacetone of formula IIa, to produce 3-(4,4,4-trifluoro-3-oxo-1-butenyl)benzonitrile of formula IIIa, according to the following scheme:

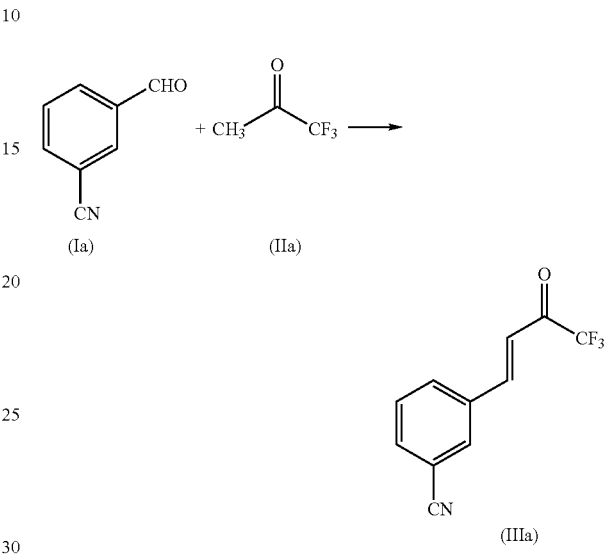

3-cyanobenzaldehyde in dichloromethane was cooled to 0–10° C., and an amine reagent such as pyrrolidine or another secondary amine such as piperidine or morpholine, or a dialkylamine such as diethylamine capable of effecting the particular transformation, was added and the reaction vessel stirred for 10 minutes or longer. 1,1,1-trifluoroacetone, or an aqueous solution thereof, was then slowly added over about 30 minutes while keeping the temperature at −5–10° C., and the vessel stirred for 3–5 hours. Trifluoroacetic acid, or another strong acid such as methanesulfonic acid, was then slowly added over a period of at least 30 minutes while maintaining the temperature at −5–10° C. The vessel was stirred for 2–10 hours and then allowed to slowly warm for 5 hours to overnight at 20–30° C. The organic solvent was extracted twice with water, 5 volumes of tert-amylmethyl ether, or another solvent such as tert-butylmethyl ether, toluene, or tert-butyl acetate, were added and the organic solvent distilled off. The contents of the vessel were then heated to 45–60° C., and about 3.5–6 volumes of iso-hexane, or another suitable solvent such as heptane, cyclohexane or octane, were slowly added over 10–40 minutes. The temperature of the mixture was maintained at 45–60° C., for 10–60 minutes, and the mixture then ramp-cooled over 30 or more minutes to 5–22° C. The reaction mixture was then stirred overnight, cooled to −3 to −8° C., and held at that temperature for 3 or more hours until the α,β-unsaturated ketone crystallized from the solvent. Solid α,β-unsaturated ketone was recovered by filtration.

Example 2

3-[(2-Oxocyclohexylidene)methyl]benzenecarbonitrile

3-[(2-Oxocyclohexylidene)methyl]benzenecarbonitrile (an α,β-unsaturated ketone) was made by reacting an aldehyde of formula Ia with a ketone of formula IIb, to form 3-[(2-oxocyclohexylidene)methyl]benzenecarbonitrile of formula IIIb as described in Example 1, according to the following scheme:

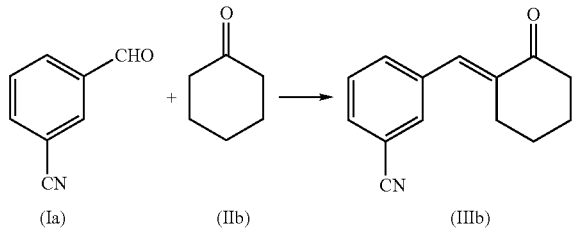

(Ia)   (IIb)   (IIIb)

To perform the reaction, the aldehyde in dichloromethane was cooled to 5° C., pyrrolidine was added, and the reaction vessel stirred for 30 minutes. The ketone was slowly added over 60 minutes while keeping the temperature at 5° C., and stirring of the vessel was continued for 3.5 hours. Trifluoroacetic acid was then slowly added over 60 minutes, the vessel stirred for 2 hours, and then allowed to warm overnight to 22° C. Purification of the product was achieved as described in Example 1. In general, α,β-unsaturated ketones may be further purified by crystallization from solvents and recovered as solids by filtration.

Example 3

(R)-3-[(1-Phenylethyl)amino]-2-cyclohexen-1-one (R)-3-[(1-Phenylethyl)amino]-2-cyclohexen-1-one, (a vinylogous amide) was made by reacting cyclohexane-1,3-dione of formula IVa with (R)-(+)-1-phenylethylamine of formula Va to form (R)-3-[(1-phenylethyl)amino]-2-cyclohexen-1-one of formula VIa, according to the following scheme:

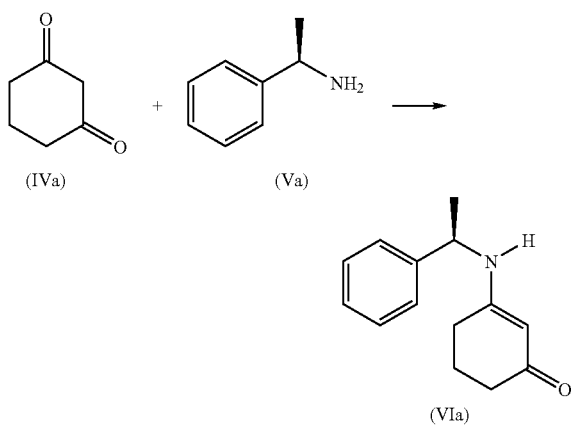

(IVa)   (Va)

(VIa)

Cyclohexane-1,3-dione and (R)-(+)-1-phenylethylamine were dissolved in acetonitrile or another inert solvent such as toluene, tetrahydrofuran or cyclohexane, heated to reflux and distilled to remove water. The vinylogous amide (R)-3-[(1-phenylethyl)amino]-2-cyclohexen-1-one was recovered as an oil by rotary evaporation of the solvent.

Alternatively, (R)-(+)-1-phenylethylamine was added to cyclohexane-1,3-dione in an inert solvent at 20–40° C., held at that temperature for about 2 hours and then refluxed to remove water.

Example 4

Vinylogous Amides

Generally vinylogous amides may be made by reacting a substituted cyclohexanone with a substituted phenylethylamine in an inert solvent such as acetonitrile and refluxing the mixture to remove water. Generally, vinylogous amides may be recovered by evaporation of the solvent to yield the product as an oil.

Example 5

3-[4,4,4-Trifluoro-3-oxo-1-[2-oxo-6-(1-phenylethylimino)cyclohexyl]-butyl]benzonitrile 3-(4,4,4-Trifluoro-3-oxo-1-butenyl)benzonitrile of formula IIIa from Example 1, was reacted with (R)-(+)-[(1-phenylethyl)amino]-2-cyclohexen-1-one of formula VIa from Example 3, to form 3-[4,4,4-trifluoro-3-oxo-1-[2-oxo-6-(1-phenylethylimino)cyclohexyl]butyl]benzonitrile of formula VIIa (a 1,5-diketone), according to the following scheme:

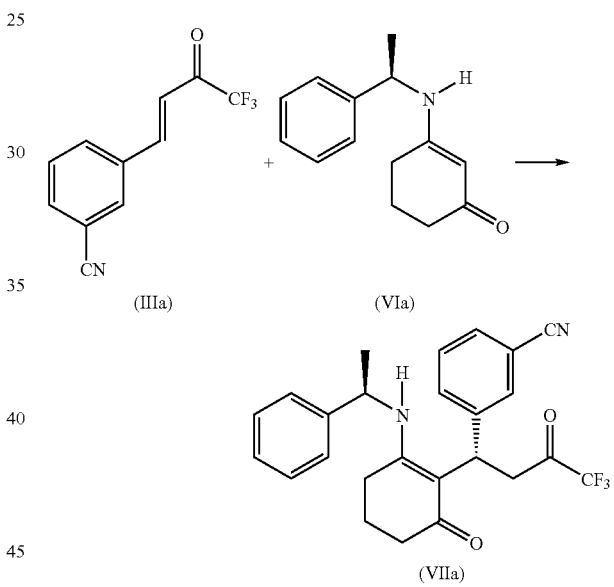

(IIIa)   (VIa)

(VIIa)

The α,β-unsaturated ketone (IIIa, 1.0 equivalent) was added to a solution of vinylogous amide (VIa, 1.0 equivalent) in acetonitrile so that the volume-ratio of acetonitrile to α,β-unsaturated ketone was about 3.5–1.0. Trimethylsilyl chloride (0.8–1.2 equivalents) was added dropwise over 1–30 minutes and the solution heated and maintained at 40–50° C., for 12 hours or more to yield the 1,5-diketone.

Example 6

(−)-4-(3-Cyanophenyl)-2-trifluoromethyl-4,6,7,8-tetrahydro-5(1H)-quinolone (−)-4-(3-Cyanophenyl)-2-trifluoromethyl-4,6,7,8-tetrahydro-5(1H)-quinolone was made by converting the 1,5-diketone of formula VIa, from Example 5, to a hemiaminal of formula VIIb, and thence to (−)4-(3-cyanophenyl)-2-trifluoromethyl-4,6,7,8-tetrahydro-5(1H)-quinolone of formula VIIa (a 1,4-dihydropyridine), according to the following scheme:

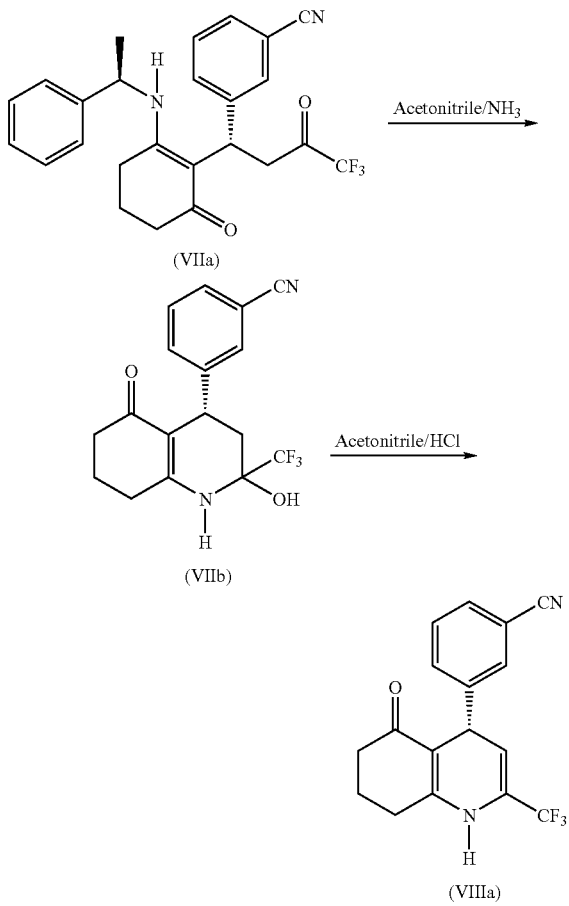

(VIIa)

Acetonitrile/NH₃

(VIIb)

Acetonitrile/HCl (VIIIa)

The solution from example 5 was cooled, aqueous ammonia (at least 10.7 equivalents) was added and the mixture heated to 40–60° C., for 5–17 hours to generate the hemiaminal. VIIb. The reaction mixture was then cooled to 20° C., and an acid selected from methane sulfonic acid, trifluoroacetic acid, acetic acid, para-toluene sulfonic acid, AMBERLYST™ 15 (ion exchange resin), or concentrated hydrochloric acid (5–8 equivalents) was slowly added in small portions over at least 30 minutes while maintaining the temperature at 0–30° C. The organic solution was brine-extracted and then heated to reflux for 410 hours to convert the hemiaminal to the 1,4-dihydropyridine. The acetonitrile was removed and replaced with dichloromethane, which was washed first with water and then with aqueous sodium hydroxide. The dichloromethane was evaporated, the solid residue taken up in acetonitrile, the solution concentrated and cooled to crystallize the title compound which was recovered by filtration.

Example 7

Process for Making of
3-(4,4,4-trifluoro-3-oxo-1-butenyl)benzonitrile

A standard 4-necked 1000 mL round bottomed flask (vessel A) equipped with overhead stirrer, condenser and temperature probe, is charged with 3-cyanobenzaldehyde (30.0 g at 100%, 0.229 mole, 1.0 equivalent) under a slow stream of nitrogen;

dichloromethane (120 mL, 4 volumes) is charged into vessel A, with agitation and the mixture allowed to stir for 10–30 minutes at 20–30° C.;

the reaction mixture is cooled to 0–10° C.;

a pressure-equalized dropping funnel (Vessel B) is charged with pyrrolidine (17.9 g at 100%, 0.252 mole, 1.1 equivalents) which is transferred into vessel A over about 30 minutes at 0–10° C.;

vessel B is line washed with dichloromethane (15 mL, 0.5 volumes) into vessel A which is then stirred for about 30 minutes at 0–10° C.;

a pressure-equalized dropping funnel (Vessel C) is charged with 1,1,1-trifluoroacetone (31.01 g at 100%, 0.275 mole, 1.2 equivalents) which is transferred into vessel A over 30–60 minutes at −5 to 10° C.;

vessel A is stirred for 3–5 hours at −5–10° C. and sampled to ensure that the reaction is complete;

a pressure-equalized dropping funnel (Vessel D) is charged with trifluoroacetic acid (31.35 g at 100%, 0.275 mole, 1.2 equivalents) which is transferred to vessel A over 30–90 minutes at −5 to 10° C.;

vessel A is stirred at −5 to 10° C. for 2–10 hours, then allowed to slowly warm to 20–30° C. in about 5 hours or overnight;

the mixture is assayed to ensure that the reaction is complete;

water (150 mL (about 5 volumes)) is charged into vessel A and the vessel agitated for about 20 minutes and the mixture allowed to separate into two phases;

the lower organic phase is recovered and re-extracted twice again with water (150 mL) and the organic dichloromethane-containing phase charged into vessel A;

vessel A is set for atmospheric distillation under a slow stream of nitrogen and ⅔ of the flask volume is distilled off;

tert-amylmethylether (150 mL, 5 volumes) is charged into vessel A and the contents are set to distill at atmospheric pressure;

distillation is continued until the volume in vessel A is approximately 80 mL when the vacuum is released and the contents are heated to 45–60° C.;

a pressure-equalized dropping funnel (Vessel E) is charged with iso-hexane (150 mL, (about 3.5–6 volumes)) which is charged into vessel A over 40 minutes;

the contents of vessel A are maintained at 45–60° C. for a further 60 minutes, then ramp-cooled over 30–90 minutes to 5–22° C., and the reaction mixture is stirred overnight;

the contents of vessel A are cooled to −3 to 8° C. for about 3 hours or longer;

the resultant crystalline solid α,β-unsaturated ketone is recovered by filtration;

the filter cake is fully deliquored and dried in a vacuum oven at 50° C. until constant weight is achieved.

Example 8

Process for Making a 1,5-Diketone

A vinylogous amide in acetonitrile (2.1 volumes, 1 equivalent) is charged into a clean dry 500 mL flask, (Vessel A), inerted under nitrogen;

an α,β-unsaturated ketone (1 equivalent) is charged portionwise into vessel A;

acetonitrile (1.4 volumes) is charged into vessel A;

trimethylsilylchloride (0.82 equivalent) is charged into vessel A dropwise over about 30 minutes while keeping the temperature at 15–25° C.;

vessel A is heated at a rate of about 0.5° C. per minute to a temperature of about 45° C. and maintained at that temperature for 24 hours;

vessel A containing the 1,5-diketone is cooled to 20° C., or less.

Example 9

Process for Converting a 1,5-Diketone to a 1,4-Dihydropyridine

The reaction mixture from Example 8, is transferred into a 1000 mL 4-necked flask, vessel A;

35% aqueous ammonia (at least 10.7 equivalents) is charged into vessel A dropwise over 30 minutes while maintaining the temperature at 20–30° C.;

vessel A is heated at a rate of 0.5° C. per minute to a temperature of 40–60° C. and held in that temperature range for 17 hours;

the temperature of the batch is then held at 55° C. for about 1 hour and then cooled to 5–8° C. over about 1.5 hours;

concentrated hydrochloric acid (about 6.7 equivalents) is charged into vessel A dropwise over about 30 minutes while maintaining the temperature at 0–30° C.;

brine (1.3 volumes) is charged into vessel A;

vessel A is agitated, allowed to settle and the lower aqueous phase is discarded keeping the interface with the upper phase;

the upper acetonitrile phase is heated to reflux, maintained at reflux for 6 hours and allowed to cool overnight;

solid material is removed by filtration and the liquor is reduced to a semi-solid by rotary evaporation;

dichloromethane (at least 4 volumes) and water (at least 4 volumes) is added to the semi-solid residue and the mixture returned to vessel A;

the mixture is agitated and the lower phase is recovered;

the organic phase is extracted with water (at least 4 volumes) and recovered;

the organic phase is twice extracted with aqueous NaOH (at least 4 volumes) and then with water (at least 4 volumes) and recovered;

the organic phase is distilled at a jacket temperature of 60° C., until flow drops to a slow trickle and the head temperature falls to 25° C.;

vessel A is charged with acetonitrile (0.6–0.8 volumes) and distilled at a jacket temperature of 87° C., until the volume is reduced to 0.2–0.3 volumes;

the contents of vessel A are slowly cooled to −5 to 10° C.;

the formed solid is recovered, washed with methyl tert-butyl ether (0.1–0.2 volumes) and dried under vacuum below 70° C.

Example 10

(−)-4-(3-Cyanophenyl)-2-trifluoromethyl-4,6,7,8-tetrahydro-5(1H)-quinolone (−)-4-(3-Cyanophenyl)-2-trifluoromethyl-4,6,7,8-tetrahydro-5(1H)-quinolone of formula VIIIa, was made by reacting an α,β-unsaturated ketone of formula IIIa with an asymmetric vinylogous amide VIa of formula according to the following scheme:

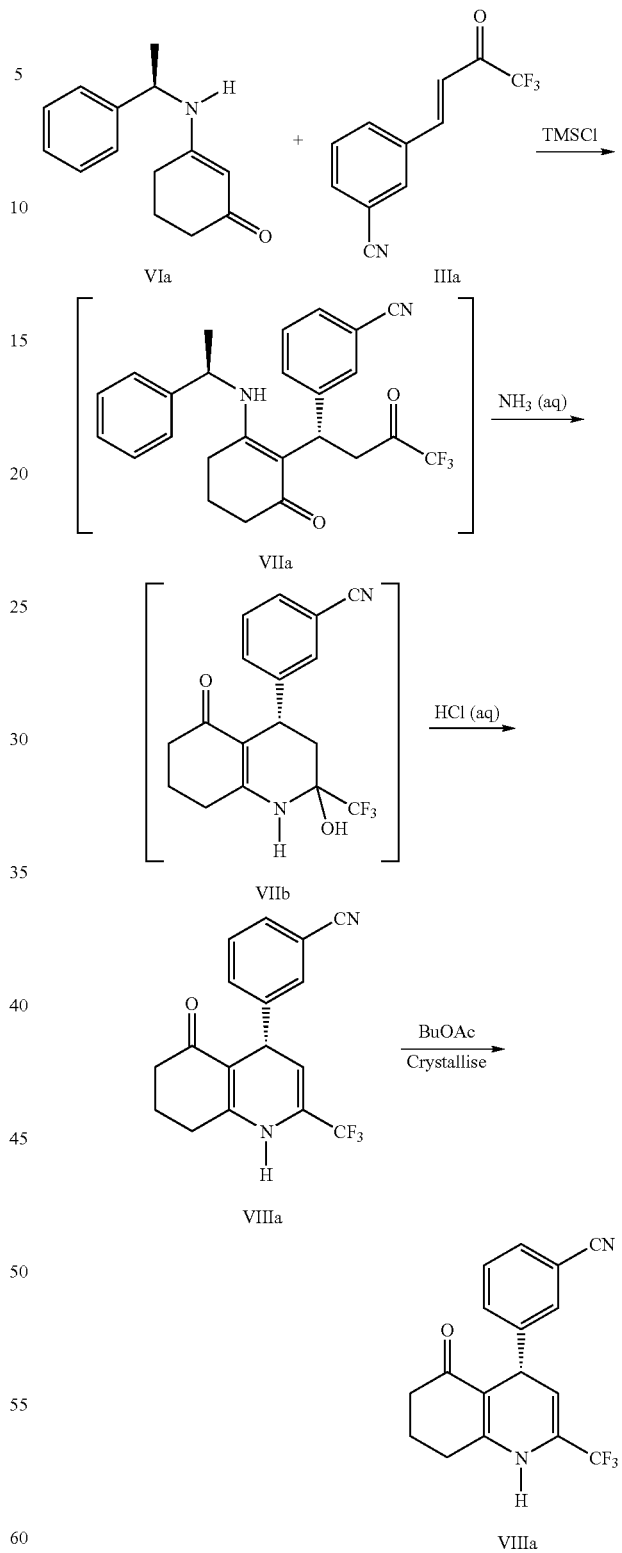

Trimethylsilylchloride, about 1.1 equivalent, was added dropwise to a solution of about 1.1 equivalent of a compound of formula VIa in acetonitrile over 25–40 minutes while maintaining the temperature at about 25° C. The solution was then cooled and about 1.0 equivalent of a solution of a compound of formula IIIa dissolved in acetonitrile was added over 25–40 minutes while maintaining the temperature at about 4–10° C. The reaction mixture was held at 5° C. for 5–10 hours, then heated to and maintained at 24–28° C. for 17–24 hours and finally heated to and maintained at 40–45° C. for 6–10 hours to form a compound of formula VIIa. The reaction mixture was then cooled to 8–15° C. and a solution of about 1.0 equivalent of ammonium chloride in about 11.0 equivalents of aqueous ammonia was added over 30–60 minutes and the mixture then heated to 50–90° C. for about 17 hours in a pressure vessel to form a compound of formula VIIb. The reaction mixture was recovered, cooled to 10–20° C. and the phases allowed to separate. The aqueous phase removed and about 1–3 equivalents of concentrated hydrochloric acid added dropwise to the organic phase over 25–40 minutes while maintaining a temperature of 10–25° C. About 300 mL of brine was then added, the mixture agitated and the aqueous phase removed after which the mixture was heated to reflux for 3–4 hours and then cooled to about 25° C. to form a compound of formula VIIIa as a solution in acetonitrile.

The compound of formula VIIIa was exchanged into about 1 equivalent of butyl acetate and the butyl acetate solution washed twice with water, twice with 2 M NaOH and once with brine. The butyl acetate phase was recovered, concentrated by evaporation under reduced pressure (60 mm Hg), cooled to room temperature over about 3 hours, then to 0° C. over about 3 hours and then held at 0° C. for about 2 hours. Crystals of the title compound were recovered by filtration, washed with methyl tert-butyl ether and dried in vacuo at 65° C. to constant weight.

The invention claimed is:
1. A process for making a 1,4-dihydropyridine, said process comprising:
  a) forming a substituted or unsubstituted substantially homo-chiral vinylogous amide by:
    (i) dissolving a substituted or unsubstituted cyclohexanone and a substituted or unsubstituted substantially homo-chiral phenylethylamine in acetonitrile;
    (ii) refluxing to remove water so as to form said vinylogous amide, and
    (iii) isolating said vinylogous amide by evaporating volatile materials;
  b) forming a substituted or unsubstituted α,β-unsaturated ketone by:
    (iv) reacting an aldehyde with a amine-reagent selected from pyrrolidine, piperidine, morpholine and diethylaminepyrrolidine in dichloromethane at a temperature of 0–10° C. to form an intermediate, and
    (v) reacting said intermediate with a substituted or unsubstituted ketone by adding trifluoroacetic acid while maintaining a temperature at 0–10° C., to form said α,β-unsaturated ketone;
  c) dissolving said vinylogous amide in acetonitrile inerted under nitrogen at a temperature about 25° C.;
  d) adding to the amide of step c) a silicon reagent selected from: trimethylsilyl chloride, triethylsilyl chloride, triphenylsilyl chloride, trimethylsilyltriflate and tributylsilyl chloride over 25–40 minutes while maintaining said temperature at about 25° C. to form a reaction mixture and maintaining said temperature at about 25° C. for about 30 minutes;
  e) cooling said reaction mixture to a temperature about 4–10° C. and adding said α,β-unsaturated ketone dissolved in acetonitrile inerted under nitrogen over 25–40 minutes while maintaining said temperature;
  f) maintaining said reaction mixture at 5° C. for 5–10 hours, then heating to and maintaining at 24–28° C. for 17–24 hours and further heating to and maintaining at 40–45° C. for 6–10 hours;
  g) cooling said reaction mixture to 8–15° C. and adding ammonia over 30–60 minutes;
  h) heating said reaction mixture to 50–90° C. for about 17 hours in a pressure vessel;
  i) recovering the acetonitrile phase and adding an acid selected from: methane-sulfonic acid, trifluoroacetic acid, acetic acid, para-toluene sulfonic acid, AMBERLYST™ 15 (ion exchange resin), and concentrated hydrochloric acid over 25–40 minutes while maintaining a temperature of 10–25° C. followed by heating to reflux to form a 1,4-dihydropyridine.

2. A process for making a 1,4-dihydropyridine comprising:
  a) forming a substituted or unsubstituted substantially homo-chiral vinylogous amide by:
    (i) dissolving a substituted or unsubstituted cyclohexanone and a substituted or unsubstituted substantially homo-chiral phenylethylamine in acetonitrile;
    (ii) refluxing to remove water so as to form said vinylogous amide, and
    (iii) isolating said vinylogous amide by evaporating volatile materials;
  b) forming a substituted or unsubstituted α,β-unsaturated ketone by:
    (iv) reacting an aldehyde with a amine-reagent selected from pyrrolidine, piperidine, morpholine and diethylaminepyrrolidine in dichloromethane at a temperature of 0–10° C. to form an intermediate, and
    (v) reacting said intermediate with a substituted or unsubstituted ketone by adding trifluoroacetic acid while maintaining a temperature at 0–10° C. to form said α,β-unsaturated ketone;
  c) dissolving said vinylogous amide in acetonitrile inerted under nitrogen at a temperature about 25° C.;
  d) adding to the amide of step c) a silicon reagent selected from: trimethylsilyl chloride, triethylsilyl chloride, triphenylsilyl chloride, trimethylsilyltriflate and tributylsilyl chloride over 25–40 minutes while maintaining said temperature at about 25° C. to form a reaction mixture and maintaining said temperature at about 25° C. for about 30 minutes;
  e) cooling said reaction mixture to a temperature about 4–10° C. and adding said α,β-unsaturated ketone dissolved in acetonitrile inerted under nitrogen over 25–40 minutes while maintaining said temperature;
  f) maintaining said reaction mixture at 5° C. for 5–10 hours, then heating to and maintaining at 24–28° C. for 17–24 hours and further heating to and maintaining at 40–45° C. for 6–10 hours;
  g) cooling said reaction mixture to 8–15° C. and adding ammonia over 30–60 minutes;
  h) heating said reaction mixture to 50–90° C. for about 17 hours in a pressure vessel; and
  i) recovering the acetonitrile phase and adding an acid selected from: methane-sulfonic acid, trifluoroacetic acid, acetic acid, para-toluene sulfonic acid, AMBERLYST™ (ion exchange resin), and concentrated hydrochloric acid over 25–40 minutes while maintaining a temperature of 10–25° C. followed by heating to reflux to form a 1,4-dihydropyridine;
wherein:
  said amine-reagent is pyrrolidine;
  said silicon reagent is trimethylsilyl chloride;

said ammonia is ammonia in an aqueous solution of ammonium chloride; and said acid is concentrated hydrochloric acid.

3. A process according to claim 2, wherein:

in step d) said silicon reagent is added over 30 minutes and said temperature is maintained at 25° C.;

in step e) said reaction mixture is cooled to 5° C. and said α,β-unsaturated ketone is added over 30 minutes;

in step f) said reaction mixture is maintained at 5° C. for 5 hours, then heated to 26° C. for 17 hours and finally heated to 43° C. for 6 hours;

in step g) said reaction mixture is cooled to 10° C. and said ammonia is added over 30 minutes;

in step h) said reaction mixture is heated to 80° C. for 17 hours in a pressure vessel, and in step i) said acid is added over 30 minutes.

4. The process according to claim 2, wherein:

said aldehyde of step (iv) is a compound of formula I $$R^1-CHO \quad (I)$$

wherein:

$R^1$ is selected from $(C_1-C_6)$alkyl, or aryl where any alkyl or aryl moiety is unsubstituted or mono-, di- or tri-substituted with moieties independently selected from hydroxy, halo, and cyano;

or $R^1$ is a group of formula X, (X)

wherein:

G and J are independently selected from hydrogen, hydroxy $(C_1-C_4)$alkoxy, nitro, cyano, $(C_1-C_4)$fluoroalkyl, $(C_1-C_4)$fluoroalkoxy, halo, $(C_1-C_4)$alkyl, $(C_1-C_4)$alkanoyl, phenyl and $(C_1-C_4)$alkylsulphonyl, or G and J taken together are $(C_1-C_4)$alkylenedioxy; or $R^1$ is 2-thienyl 4-substituted, 5-substituted or 4,5-substituted with E, or 3-thienyl or furyl 5-substituted with E where E is independently selected from a group consisting of nitro, cyano, halo, $(C_1-C_6)$alkyl, $(C_1-C_4)$ alkyl-sulphonyl and 2-thienyl, where halo comprises bromo, chloro, fluoro and iodo; or $R^1$ is a 2-pyridyl 4,5-substituted, 5-substituted or 5,6-substituted with E; or $R^1$ is a 3-pyridyl 6-substituted with E; or $R^1$ is a 4-pyridyl 2-substituted with E; said ketone is a compound of formula II (II)

wherein:

$R^2$ is selected from hydrogen, $(C_1-C_6)$alkyl and mono-, di- or tri-halo$(C_1-C_4)$alkyl;

$R^3$ is selected from hydrogen, cyano, $(C_1-C_6)$alkyl, $(C_1-C_6)$fluoroalkyl and ethanoyl; or $R^2$ and $R^3$, when taken together, form a substituted or unsubstituted $(C_1-C_6)$cycloalkyl moiety;

said cyclohexanone is a compound of formula IV (IV)

wherein:

$R^4$ and $R^5$ are independently selected from H and $(C_1-C_4)$ alkyl, and said substantially homo-chiral phenylethylamine is a compound of formula V (V)

5. The process according to claim 4, wherein:

$R^1$ is selected from $(C_1-C_6)$alkyl, or aryl where any foregoing ethyl or aryl moiety can be substituted with hydroxy, halo, or cyano;

$R^2$ is selected from mono-, di- or tri-halo$(C_1-C_4)$alkyl;

$R^3$ is selected from hydrogen, cyano, $(C_1-C_6)$alkyl, $(C_1-C_6)$fluoroalkyl and ethanoyl, and $R^4$ and $R^5$ are independently selected from hydrogen or methyl.

6. The process according to claim 4, wherein:

$R^1$ is selected from methyl, ethyl, propyl, isopropyl, butyl, iso-butyl, sec-butyl, tert-butyl, pentyl, 3-methylbutyl, 1-ethylpropyl, hexyl, 4-methylpentyl, phenyl, 3-methoxyphenyl, 3-nitrophenyl, 3-cyanophenyl, 3-trifluoromethylphenyl, 3-trifluoromethyl-4-cyanophenyl, 4-trifluoromethylphenyl, 3-trifluoromethoxyphenyl, 3-fluorophenyl, 3-chlorophenyl, 3-chloro-4-fluorophenyl, 3-bromophenyl, 4-fluorophenyl, 4-chlorophenyl, 3-bromo--4-fluorophenyl, 3,4-dichlorophenyl, 4-methylphenyl, and 3,4-methylenedioxyphenyl;

$R^2$ is selected from methyl, ethyl, propyl, iso-propyl, butyl, iso-butyl, sec-butyl, tert-butyl and trifluoromethyl;

$R^3$ is selected from hydrogen, cyano and ethanoyl, and $R^4$ and $R^5$ are selected from hydrogen and methyl.

7. The process according to claim 4, wherein:

$R^1$ is 3-cyanobenzaldehyde;

$R^2$ is trifluoromethyl, and $R^3$, $R^4$ and $R^5$ are hydrogen.

* * * * *